(12) United States Patent
Li

(10) Patent No.: US 7,186,548 B2
(45) Date of Patent: Mar. 6, 2007

(54) CELL CULTURE TOOL AND METHOD

(75) Inventor: Albert Pakhung Li, Columbia, MD (US)

(73) Assignee: Advanced Pharmaceutical Sciences, Inc., Baltimore, MD (US)

(*) Notice: Subject to any disclaimer, the term of this patent is extended or adjusted under 35 U.S.C. 154(b) by 366 days.

(21) Appl. No.: 10/751,983

(22) Filed: Jan. 7, 2004

(65) Prior Publication Data
US 2005/0101010 A1 May 12, 2005

Related U.S. Application Data

(60) Provisional application No. 60/518,331, filed on Nov. 10, 2003.

(51) Int. Cl.
C12M 1/22 (2006.01)
C12M 3/00 (2006.01)
C12N 5/02 (2006.01)

(52) U.S. Cl. ............... 435/288.5; 435/305.3; 435/288.3; 435/288.4; 435/305.1; 435/305.2

(58) Field of Classification Search ............ None
See application file for complete search history.

(56) References Cited

U.S. PATENT DOCUMENTS

| | | | |
|---|---|---|---|
| 3,826,717 A * | 7/1974 | Gilbert et al. | 435/33 |
| 4,304,865 A | 12/1981 | O'Brien | |
| 4,871,674 A | 10/1989 | Matsui | |
| 5,026,649 A | 6/1991 | Lyman | |
| 5,665,596 A | 9/1997 | Mussi | |

OTHER PUBLICATIONS

Kligerman et al., "Sister chromatid exchange studies in human fibroblast-rat hepatocytes cultures: a new in vitro system to study SCEs", Environ Mutagen 2:157-165 (1980).

Lyng et al., "Metabolic activation in the fetal mouse salivary gland culture system with rat hepatocytes, rat S-9, and human S-9", Teratog Carcinog Mutagen 11:31-39 (1991).

Ebron-McCoy et al., "Profile of procarbazine-induced embryotoxicity in an embryo hepatocytes co-culture system", Teratog Carcinog Mutag 15:33-42 (1995).

El-Mir et al., "In vitro test to determine the effect of cytostatic drugs on co-cultured rat hepatocytes and hepatoma cells", In J Exp Pathol 79:109-115, (1998).

Mangnum et al., "Co-Culture of Primary Pulmonary Cells to Model Alveolar Injury and Translocation of Protein", In Vitro. Cell Dev. Biol. 26:1135-1143 (1990).

Wang and Cynade, "Effects of astrocytes on neuronal attachment and survival shown in a serum-free co-culture system," Brain Res Brain Res Protoc., 4(2):209-16 (1999).

Okamato "Evaluation of the function of primary human hepatocytes co-cultured with the human hepatic stellate cell (HSC) line L190", Int J Artif Organs, 21(6):353-9 (1998).

Guguen-Guillouzo et al., "Hepatotoxicity and molecular aspects of hepatocyte function in primary culture", Xenobiotica, 18(6):773-83 (1988).

* cited by examiner

Primary Examiner—David Guzo
Assistant Examiner—Kimberly A Makar
(74) Attorney, Agent, or Firm—McNeely IP Law; Kevin J. McNeely

(57) ABSTRACT

A cell co-culture tool includes a body, an outer wall surrounding the body, and more than one vessel within the perimeter of the outer wall. Each vessel has a top edge below a rim of the outer wall.

A method of interacting a substance with more than one type of cell material in a culture dish having a plurality of wells includes depositing a different type of the cell material in separate wells of the culture dish, interconnecting the wells with a fluid medium, and adding the substance to the fluid medium.

15 Claims, 10 Drawing Sheets

CELL CULTURE TOOL AND METHOD

CROSS REFERENCE TO RELATED APPLICATIONS

This application claims priority from U.S. Provisional Application No. 60/518,331 filed Nov. 10, 2003, which is incorporated herein by reference.

FIELD OF THE INVENTION

This invention relates to tissue culture vessels and, more particularly, comprises a new and improved tissue culture vessel for co-culturing of multiple types of cells and tissues and the application of the cell culture device in biological studies, including application in drug discovery and development.

BACKGROUND OF THE INVENTION

Culture tools, such as, for example, dishes, plates, flasks, and other types of vessels, are widely used in the laboratory for a variety of purposes. In normal use, cell and tissue culturing involves the use of agar or medium, which covers the bottom of a well. Cells are routinely cultured in research laboratories for basic biochemical and cell biology research to further understand natural biological processes. Recently, cell culture systems have been used in drug discovery and development in order to test for pharmacological and toxicological effects of drug candidates. This work generally is a monoculture test process, i.e., cells of one type are grown in a suitable medium in a tissue culture vessel such as a well, a plate, or a flask.

A normal cell culture plate consists of a chamber with a flat bottom surrounded by vertical walls to allow filling of the chamber with liquid and a removable cover to retain humidity and to protect against contamination. As shown in FIGS. 1A and 1B, a commonly used multi-well plate 100 has six identical wells 110. Although the wells 110 can be formed integrally, as by injection or blow molding for example, a preferred method of manufacture is to form the plate 100 with an upper tray 120 which defines the volume contained in each well and a lower or bottom tray 130 which defines the bottom surface of each well. The well 110 depth, together with the diameter of the well 110, determines the fluid capacity of each well 110. Typically for example, each well 110 in a six well plate is about 0.35 cm. in diameter and 2.0 cm. deep, and the wells are preferably arranged in a 2 by 3 regular rectangular array.

As shown in FIG. 1B, cells 140 are deposited in the bottom of each of the wells 110. A fluid 150 is then added to cover the cells 140.

Cell culture systems, commonly known as in vitro systems, are used extensively in drug discovery and development for the evaluation of drug properties. For instance, cell culture systems are used to evaluate drug efficacy, drug metabolism, or drug toxicity. However, it is also recognized that an in vitro system may not accurately predict in vivo effects due to the lack of the complexity and interplay of biological processes in in vitro systems. For instance, by using primary liver cells (hepatocytes) in culture, the effect of a substance on liver cells can be evaluated. However, in vivo, the substance may be metabolized by other organs such as the kidneys, and the resulting metabolite may have a different effect on liver cells which would not be detected by using liver cells alone. For this reason, interest has developed in the co-culture of cells. Co-culturing involves growing one population of cells in the presence of another population of cells. Cell co-culturing has been applied in a myriad of biological studies. In pharmacology and toxicology, co-culturing of a target cell, such as, for example, cancer cells, with cells from a critical organ, such as, for example, the liver, allows the evaluation of the effect of a chemical on the target cells after its modification by cells from the critical organ, such as, for example, liver metabolism of a specific drug or drug candidate. Using the normal cell culture plate, co-culture methods are achieved by mixing the different cell types or by the use of membranes to allow two cell types to be cultured on both sides of the membrane. Evaluation of the individual cell types after being physically mixed or by using membranes can be highly difficult and tedious. Thus, a need exists for a new cell culture tool that facilitates cell co-culturing.

SUMMARY OF THE INVENTION

In one general aspect, a cell culture tool includes a body, an outer wall extending from the body, and more than one vessel defined by the configuration of the body. Each vessel has a top edge below a rim of the outer wall.

Implementation may include one or more of the following features. For example, the body may have a flat surface with each vessel comprising a depression in the flat surface of the body, the depression configured to contain a volume of fluid. The vessel may have a cylindrical wall and a circular bottom and the outer surface of the body may be in the shape of a rectangular plate. The height of the outer wall may be about 20 millimeters.

In one implementation, each vessel comprises a cup connected to the body, each cup having a top edge below the rim of the outer wall. In another implementation, the vessel includes a container having a container wall with a top edge, the height of the container wall being about 4 millimeters. In a further implementation, each vessel comprises a partition wall dividing the space defined within the perimeter of the outer wall, the partition wall having a top edge.

In another general aspect, a multi-well culture dish includes a base having a flat surface with a plurality of wells and an outer wall surrounding the base. Each of the wells includes a containing wall with a height lower than the height of the outer wall. Implementation may include one or more of the features described above and the dish may also include six wells.

In another general aspect, multiple culture vessels can be connected using tubings, with or without a device (e.g. a pump) to circulate the fluid.

In another general aspect, a method of interacting a substance with more than one type of cell material in a culture dish having a plurality of wells includes depositing a different type of the cell material in separate wells of the culture dish, interconnecting the wells with a fluid medium, and adding the substance to the fluid medium. In various implementations, the substance may include a chemical or a drug.

In another general aspect, a method of metabolizing a drug in a multi-well culture dish includes depositing different types of cell material in separate wells of the multi-well culture dish, connecting the separate wells with a fluid media, and introducing the drug into the fluid media.

Implementation may include one or more of the following features or any of the features described above. For example, the cell material may include liver, kidney, spleen or lung cells, any cells that can be cultured, and/or tissue fragments or fractions.

In another general aspect, a method of metabolizing a drug in a cell culture dish having a body with six wells and a wall surrounding the six wells includes depositing kidney cells in a first of the six wells, liver cells in a second of the six wells, heart cells in a third of the six wells, lung cells in a fourth of the six wells, spleen cells in a fifth of the six wells, and brain cells in a sixth of the six wells, filling the dish with a fluid medium to fluidly interconnect the six wells, and introducing the drug into the fluid medium.

In another general aspect, a method of co-culturing different cells in individual wells includes overfilling each well to fluidly interconnect the wells so the different cells in the individual wells communicate through a common fluid medium.

The method may include various implementations. For example, the different cells in the individual wells comprise liver cells in a first well, kidney cells in a second well, heart cells in a third well, spleen cells in a fourth well, brain cells in a fifth well, and lung cells in a sixth well. In another implementation, the different cells in the individual wells comprise liver cells in a first, second and third well and heart cells in a fourth, fifth, and sixth well. In a further implementation, the method includes introducing a substance into the common fluid medium so that the different cells in the individual wells are in contact with the same substance.

In another general aspect, a method of testing the safety and efficacy of a drug in a culture dish having separate wells includes depositing different cells of an organism in the separate wells of the culture dish, depositing a harmful agent in another of the separate wells, interconnecting the separate wells with a fluid medium, and introducing a dose of the drug into the fluid medium.

The method may include one or more of the following features or any of the features described above. For example, the method may include determining whether the different cells of the organism are harmed by the dose of the drug, determining whether the harmful agent is diminished by the dose of the drug, and/or increasing the dose of the drug if the different cells of the organism are not harmed and the harmful agent is not diminished.

The harmful agent may include tumor cells and the drug may include an anti-tumor medication. The different cells of the organism may include liver, kidney, heart, lung, spleen, and/or brain cells of the human body.

The method may further include increasing the dose of the drug until the drug harms the different cells of the organism and designating the dose of the drug at which the different cells of the organism are harmed as a toxic dose level. The method also may include increasing the dose of the drug until the effect of the harmful agent is reduced and designating the dose of the drug at which the effect of the harmful agent is reduced as an effective dose level.

The harmful agent may be cholesterol, the drug may be an anti-cholesterol drug, and the different cells may include liver cells. In another implementation, the harmful agent includes cancer cells and the drug is an anti-cancer medication that has an undesirable toxicity above a certain dose.

In another general aspect, a method of co-culturing cells in a multi-well dish includes culturing a first cell type in a first well of the multi-well dish and culturing a second cell type in a second well of the multi-well dish. The cells cultured in the second well may provide metabolites that benefit the growth of the first cell type.

In another general aspect, a method of evaluating whether a first cell type can enhance the growth of a second cell type includes culturing the first cell type in a first well, culturing the second cell type in a second well, fluidly interconnecting the first well and the second well, and examining the impact of the cultured first cell type on the growth of the second cell type.

The cell culture tool provides a convenient way for multiple cell types to be co-cultured but yet physically separate so that the individual cell types can be evaluated separately after co-culturing in the absence of the co-cultured cells.

The tool allows the culturing of cells in individual wells under different conditions, such as, for example, different attachment substrate, different media, or different cell types, followed by allowing the different wells to intercommunicate via a common medium. After culturing as an integrated culture with a common medium, the medium can be removed, and each well can be subjected to independent, specific manipulations, such as, for example, lysis with detergent for the measurement of specific biochemicals or fixation and staining for morphological evaluation.

As described above in the method, an application is the culturing of multiple primary cells from different organs (e.g. liver, heart, kidney, spleen, neurons, blood vessel lining cells, thyroidal cells, adrenal cells, iris cells, cancer cells) so the plate, after the establishment of individual cell types and flooding, represents an in vitro experimental model of a whole animal. Another application of the culture tool is to evaluate the effect of a substance on multiple cell types. In drug discovery and development, this culture system can be used to evaluate metabolism of a new drug or drug candidate by cells from multiple organs or the effect of a drug or drug candidate on the function and viability of cells from multiple organs. An example of this application is to culture cells from multiple organs along with tumor cells, followed by treatment of the co-culture with an anticancer agent to evaluate toxicity of the agent to the cells of the different organs in comparison with its toxicity towards the cancer cells to evaluate the therapeutic index of the agent. In other words, each plate simulates the treatment of a whole animal with the anticancer agent followed by examination of each organ. Multiple tumor cell types can also be used to evaluate the efficacy of the tested drug or drug candidate on different types of tumors.

The tool can be utilized for the culturing of cells which require exogenous factors from other cell types without physically mixing the cell types, as the different cell types are placed in different wells, with the overlaying medium allowing the exchange of metabolites and/or secreted biomolecules.

Figure 1A:
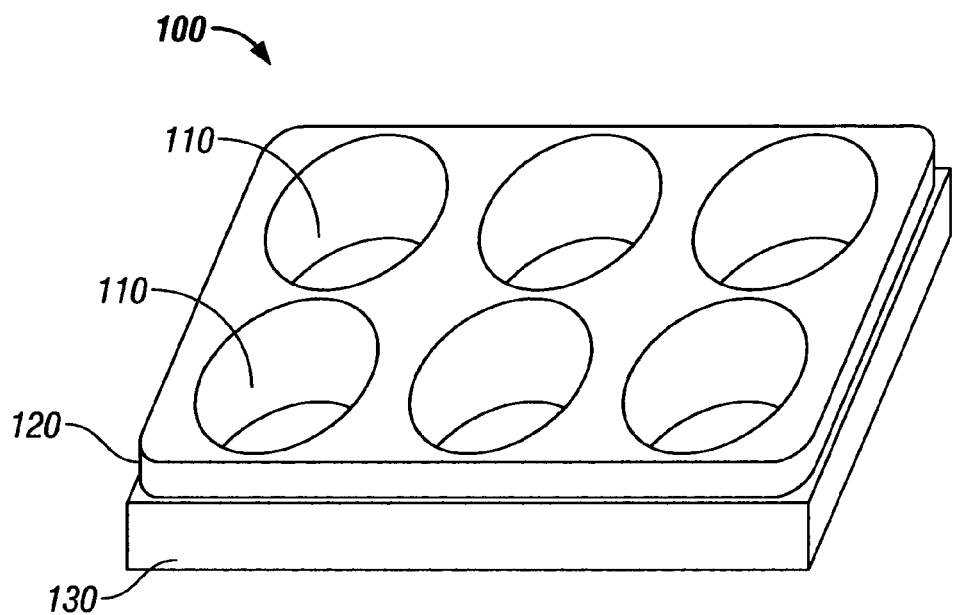
FIG. 1A is a perspective view of a conventional multi-well culture plate.
Figure 1B:
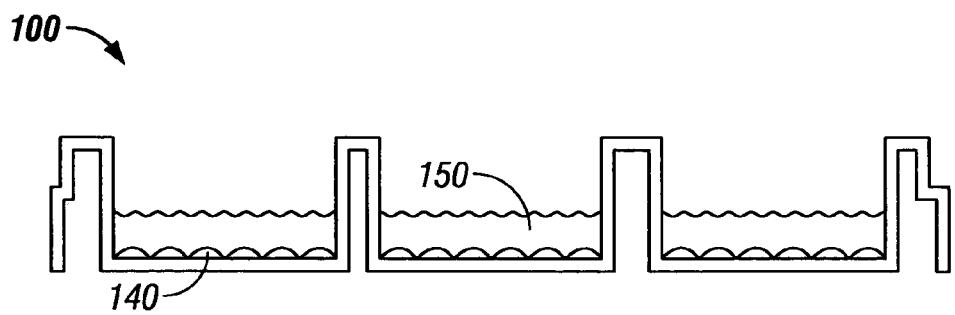
FIG. 1B is a cross-section view of the conventional multi-well culture plate shown in FIG. 1A.

Reference numerals in the drawings correspond to numbers in the Detailed Description for ease of reference.

DETAILED DESCRIPTION

Implementations of the tool 200, 300, 400 embodying the current invention are shown in FIGS. 2A–5B and FIG. 10. The tool 200, 300, 400 includes multiple wells within each a type of cells can be cultured, but each well can be overfilled or flooded, so that the cells in the different wells can share a common medium. This is achieved by configuring each well as an indentation inside a larger plate (FIGS. 2A and 2B), placing short partitions inside a larger plate (FIGS. 3A and 3B), or placing small inserts inside a larger plate (FIGS. 4A and 4B). However, this invention can be applied to any multi-well format with any number of wells per plate.

Figure 2A:
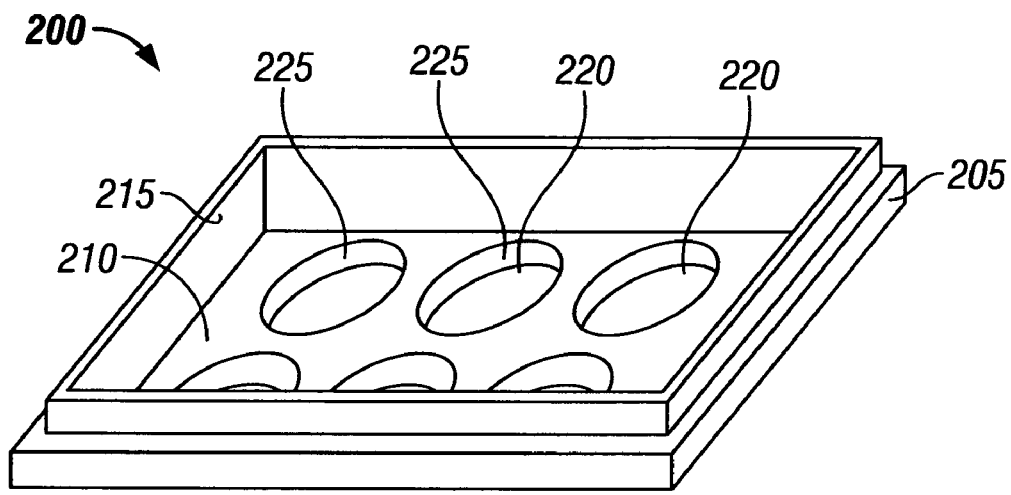
FIG. 2A is a perspective view of a cell culture tool.
Figure 2B:
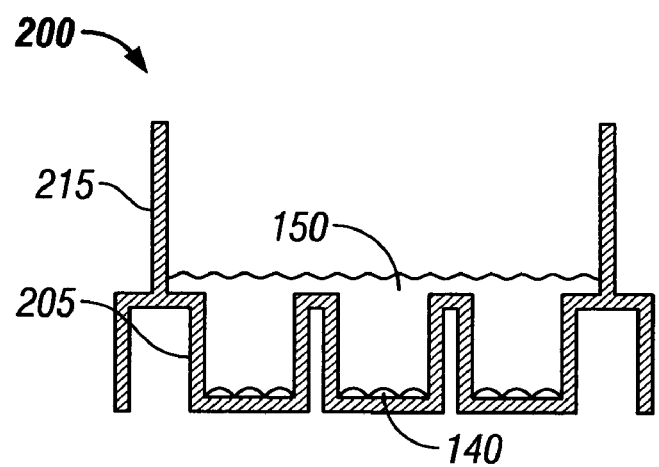
FIG. 2B is a cross-section view of the cell culture tool shown in FIG. 2A.

Referring to FIGS. 2A and 2B, a multi-well tool 200 of the present invention comprises a body 205 having a substantially planar top surface 210, and an outer wall 215 extending from the body 205. Six wells 220 are formed in the body 205 by depressions in the top surface 210. Each well 220 has a containing wall 225 that may slant downward from or be perpendicular to the flat surface 210.

The overall dimensions of the tool 200 may be about 12.60 cm long and 8.40 cm wide. The body 205 may have a height of 0.20 cm, with the outer wall 215 extending upward from the flat surface 210 approximately 0.15 cm. The height of each containing wall 225 may be 0.05 cm. The wells 220 are configured in a regular array and are separated by approximately 0.02 cm. In another implementation (not shown), the wells are equi-distant from each other by positioning the wells around a circumference of a circle. The dimensions of the tool 200 are merely illustrative, however, the tool 200 is configured to allow overfilling of each well 220 in order to interconnect the wells 220 in a common fluid media while preventing the cells in the individual wells 220 from drowning.

Figure 3A:
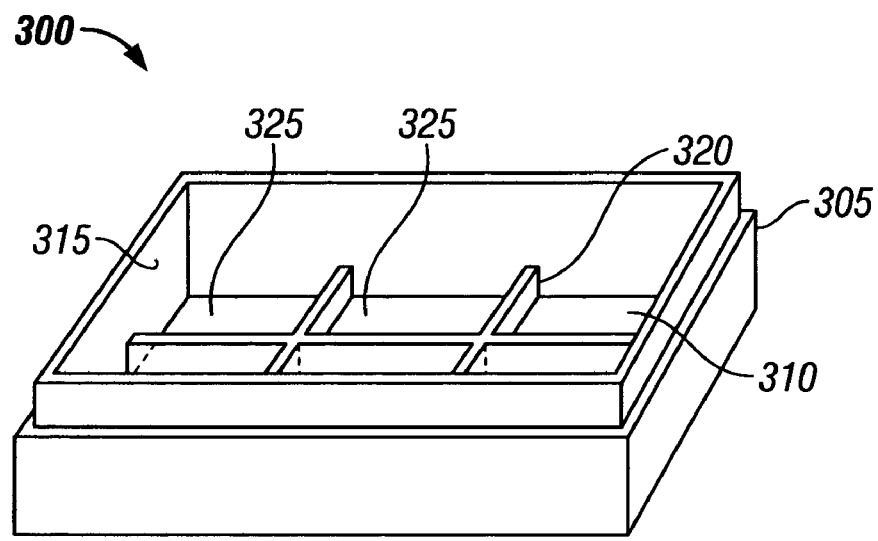
FIG. 3A is a perspective view of another embodiment of a cell culture tool.
Figure 3B:
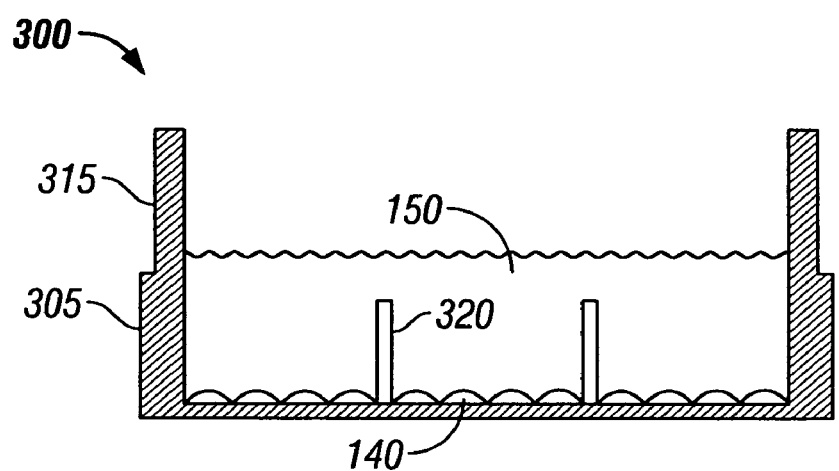
FIG. 3B is a cross-section view of the cell culture tool shown in FIG. 3A.

Referring to FIGS. 3A and 3B, a multi-well tool 300 includes a body 305 having a planar top surface 310, surrounded by an outer wall 315. Partitions 320 are positioned on the top surface 310 to divide the space bounded by the outer wall 315 into six wells 325. The outer wall 315 extends upward 0.15 cm from the top surface 310 and the height of the partitions is approximately 0.05 cm. Thus, each well 325 can be overfilled to interconnect the wells 325 in a fluid medium.

The partitions 320 may be bonded to the top surface 310 and the outer wall 315. In another implementation, the partitions 320 may be removable.

Figure 4A:
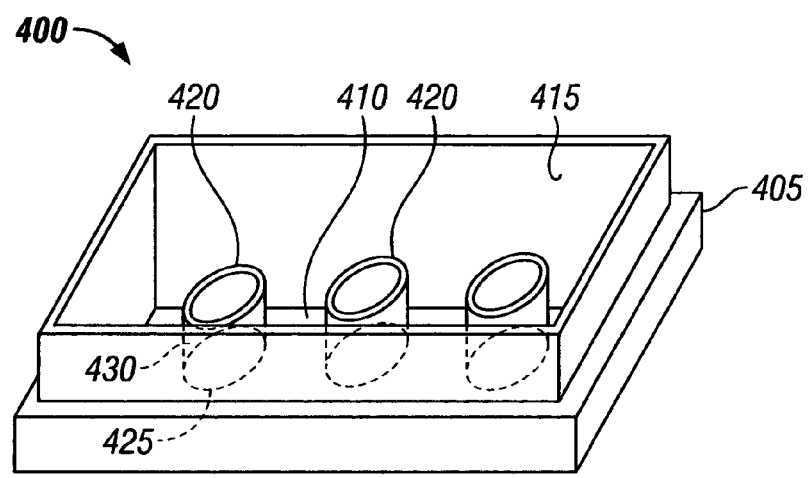
FIG. 4A is a perspective view of a further embodiment of a cell culture tool.
Figure 4B:
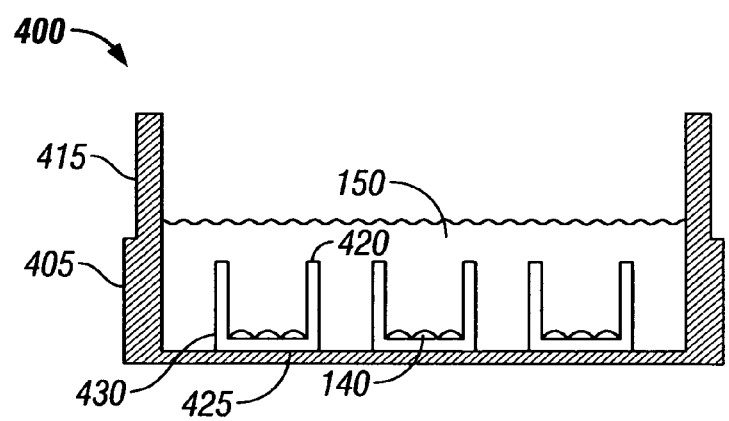
FIG. 4B is a cross-section view of the cell culture tool shown in FIG. 4A.
Figure 5A:
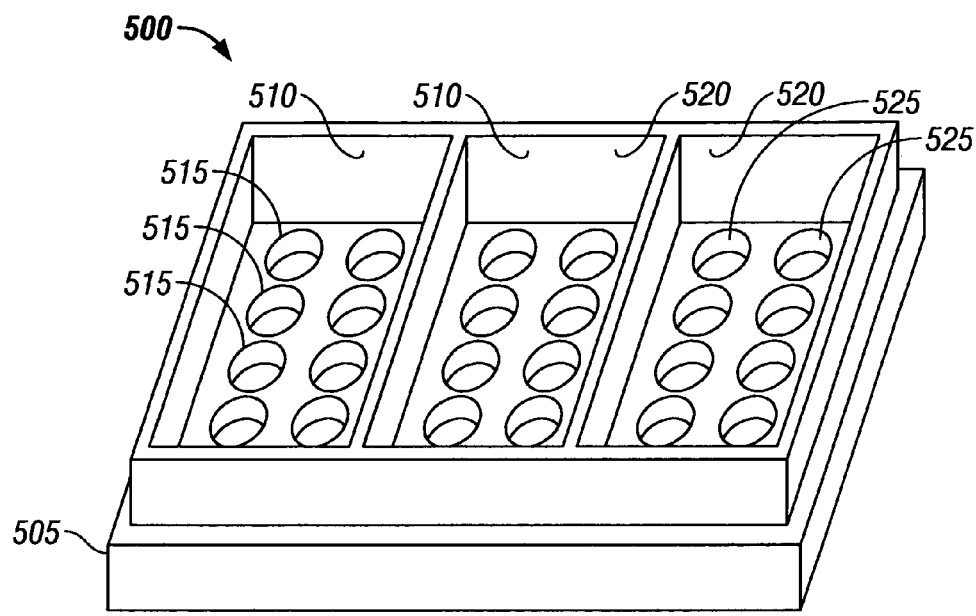
FIG. 5A is a perspective view of a cell culture tool with separate chambers and multiple wells per chamber.
Figure 5B:
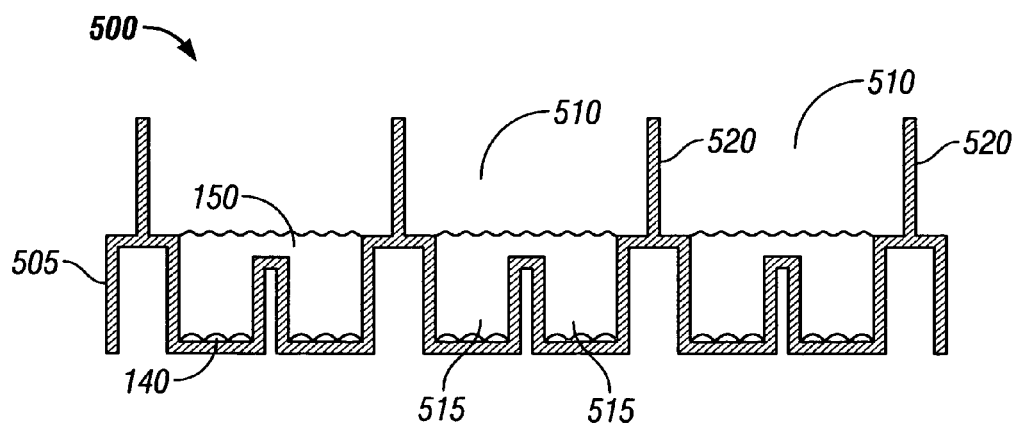
FIG. 5B is a cross-section view of the cell culture tool shown in FIG. 5A.

Referring to FIGS. 4A and 4B, a multi-well tool 400 includes a body 405 having a planar top surface 410, surrounded by an outer wall 415. Inserts 420 are placed on the flat surface 410, with each insert defined by a bottom 425 and a containing wall 430. The height of the containing wall is about 0.05 cm and the height of the outer wall extends 0.15 cm from the top surface 410. In other implementations, the inserts 420 may comprise cups, dishes, or a tray that may be removed from the top surface 310.

The multi-well plates as described in FIGS. 2A–4B can be grouped to form a cell culture tray 500 as a single body 505 with multiple compartments or chambers 510 (FIGS. 5A and 5B), each compartment 510 having multiple wells 515, to allow experimentation with different cell selections, liquid medium, or a different exogenous substance in each compartment. Limiting walls 520 surrounding each compartment 510 are higher than the containing walls 525 of the individual wells 515 within that compartment 510, with the limiting walls 520 having a height of 0.20 cm and each well 515 inside the larger body 505 having a height of 0.04 cm.

The tool 200-500 may be formed of various suitable materials. In one implementation, the tool 200-500 is formed of a substantially rigid, water-insoluble, fluid-impervious, typically thermoplastic material substantially chemically non-reactive with the fluids to be employed in the assays to be carried out with the tool 200-500. The term "substantially rigid" as used herein is intended to mean that the material will resist deformation or warping under a light mechanical or thermal load, which deformation would prevent maintenance of the substantially planar surface, although the material may be somewhat elastic. Suitable materials include, for example, polystyrene or polyvinyl chloride with or without copolymers, polyethylenes, polystyrenes, polystyrene-acrylonitrile, polypropylene, polyvinylidine chloride, and the like. Polystyrene is a material that can be used as it is the common polymer used for cell culture vessels, inasmuch as it characterized by very low, non-specific protein binding, making it suitable for use with samples, such as, for example, blood, viruses and bacteria, incorporating one or more proteins of interest. Glass is also a suitable material, being used routinely in cell culture vessels and can be washed and sterilized after each use.

Figure 6:
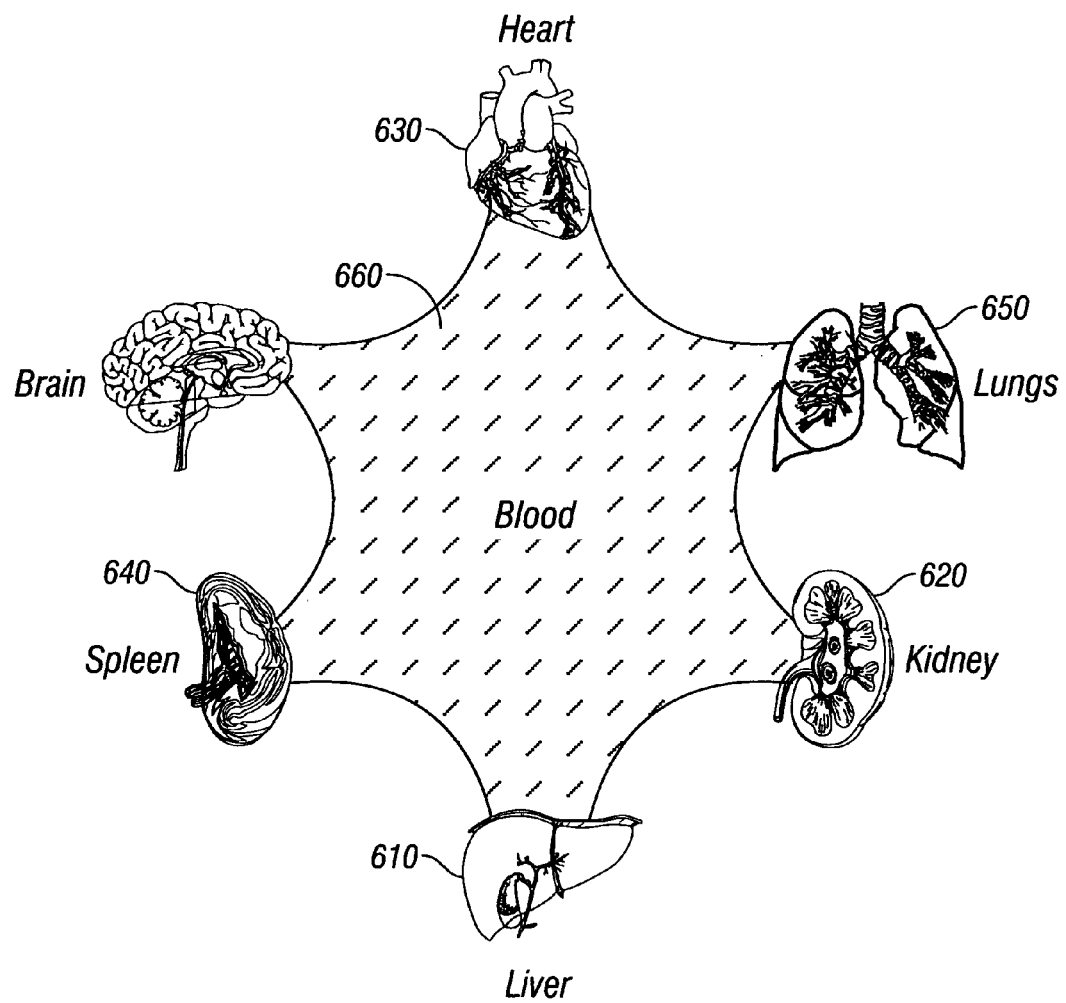
FIG. 6 shows part of an organ system of an animal.
Figure 7:
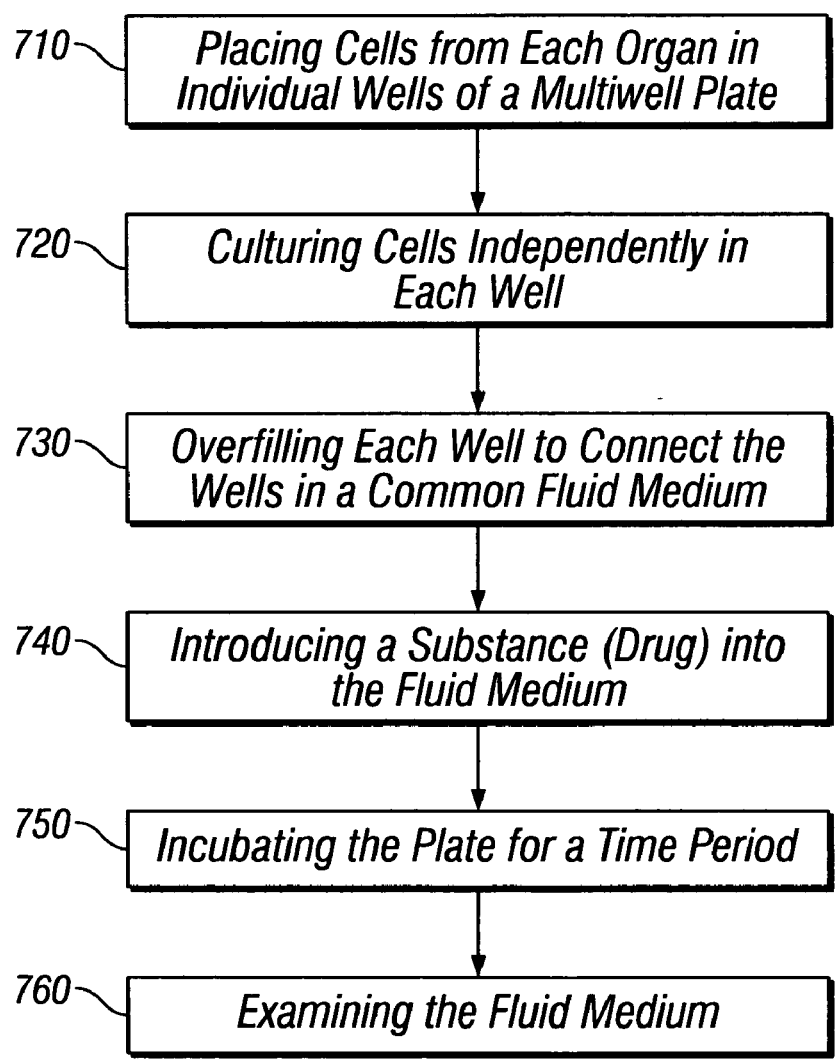
FIG. 7 is a flow diagram of evaluating metabolism of an exogenous substance by multiple cell types.

The cell culture tool can be used to test drug metabolism. As shown in FIG. 6, the major organs that are known to metabolize drugs are the liver 610, intestines and kidneys 620, whereas other organs such as the heart 630, spleen 640, lungs 650, and blood vessels 660 also possess specific metabolizing pathways. Referring to FIG. 7, method of using the cell culture tool includes evaluating metabolism of an exogenous substance by multiple cell types 700. Using the tool, the cells from major organs including the liver, intestines, kidneys, heart, spleen, lungs, and brain are placed in the multiple well plate, with cells from each organ placed separately in individual wells (operation 710). For instance, in the six-well format, liver cells are placed in well 1, intestines in well 2, kidneys in well 3, heart in well 4, spleen in well 5 and lungs in well 6. Each cell type can be cultured (operation 720) using different attachment substrate and culture medium, for instance, liver cells are best cultured on collagen and require supplementation with insulin and dexamethasone, spleen cells are cultured in agar suspension, etc. After each cell type is established, the plate can be "flooded" by overfilling each well (operation 730), with the cells from the different wells sharing a common liquid medium. The exogenous substance, such as, for example, a drug, a drug candidate, an environmental pollutant, or a natural product, can be added to the medium (operation 740) and incubated for specific time periods (operation 750). After incubation, the medium can be collected for the examination of the extent of metabolism (how much of the parent substance is remaining), or metabolic fate (what are the identities of the metabolites), using established analytical methods (operation 760).

Figure 8:
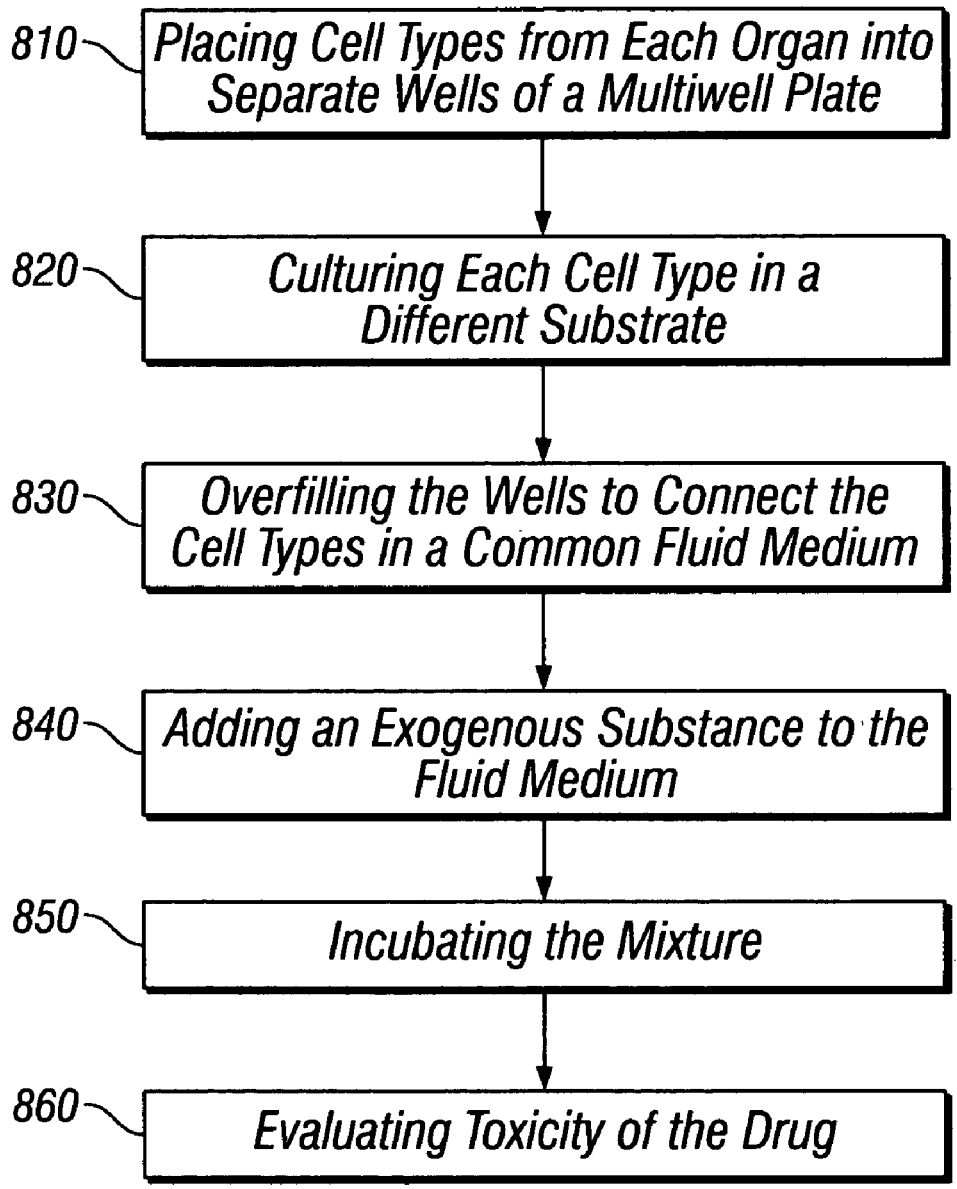
FIG. 8 is a flow diagram of evaluating the toxicity of an exogenous substance on multiple cell types.

Referring to FIG. 8, another method 800 of using the cell culture tool includes evaluating the toxicity of an exogenous substance on multiple cell types. The major organs that are susceptible to drug toxicity are the liver, intestines, kidneys, heart, spleen, lungs, and brain. Using the tool, the cells from the liver, intestines, kidneys, heart, spleen, lungs, brains and blood vessels, are placed in the multiple well plate (operation 810). Cells from each organ are placed in individual wells. For instance, in an eight-well format, liver cells are placed in well 1, intestines in well 2, kidneys in well 3, heart in well 4, spleen in well 5, lungs in well 6, brain in well 7, and blood vessels in well 8. Each cell type can be cultured using a different attachment substrate and culture medium (operation 820), for instance, liver cells are best cultured on collagen and require supplementation with insulin and dexamethasone, spleen cells are cultured in agar suspension, etc. After each cell type is established, the plate can be "flooded" by overfilling each well, with the cells from the different wells sharing a common liquid medium (operation 830). The exogenous substance, such as, for example, a drug, a drug candidate, an environmental pollutant, or a natural product, is added to the medium (operation 840). The mixture is then incubated for specific time periods (operation 850). After incubation, the medium can be removed, and each individual cell type can be evaluated for toxicity (operation 860) morphologically, such as, for example, microscopic analysis, and by a biochemical analysis, such as, for example, lysed with detergent for the measurement of ATP content of the cells in each individual well.

The cell culture tool can also be used to evaluate drug efficacy and safety. In drug discovery, intact cells are used as indicators of drug efficacy. For instance, liver cells are used to evaluate the effect of a drug on cholesterol synthesis in order to develop a novel inhibitor of cholesterol synthesis as a drug to lower the cholesterol level in patients with high levels of cholesterol. A culture can be applied with cells from multiple organs as described above to evaluate the effects of a drug candidate on cholesterol synthesis in multiple organs. The method can be used to evaluate efficacy, metabolism and toxicity simultaneously using the culture system.

For instance, a "therapeutic index" of a potential new drug to treat high cholesterol levels can be evaluated by using liver cells as indicator cells to determine the effectiveness and toxicity of the drug. Efficacy can be measured in the presence of metabolism of all key cell types, thereby mimicking an in vivo situation where metabolism may lower the efficacy (or increase the efficacy) of the new drug.

Figure 9:
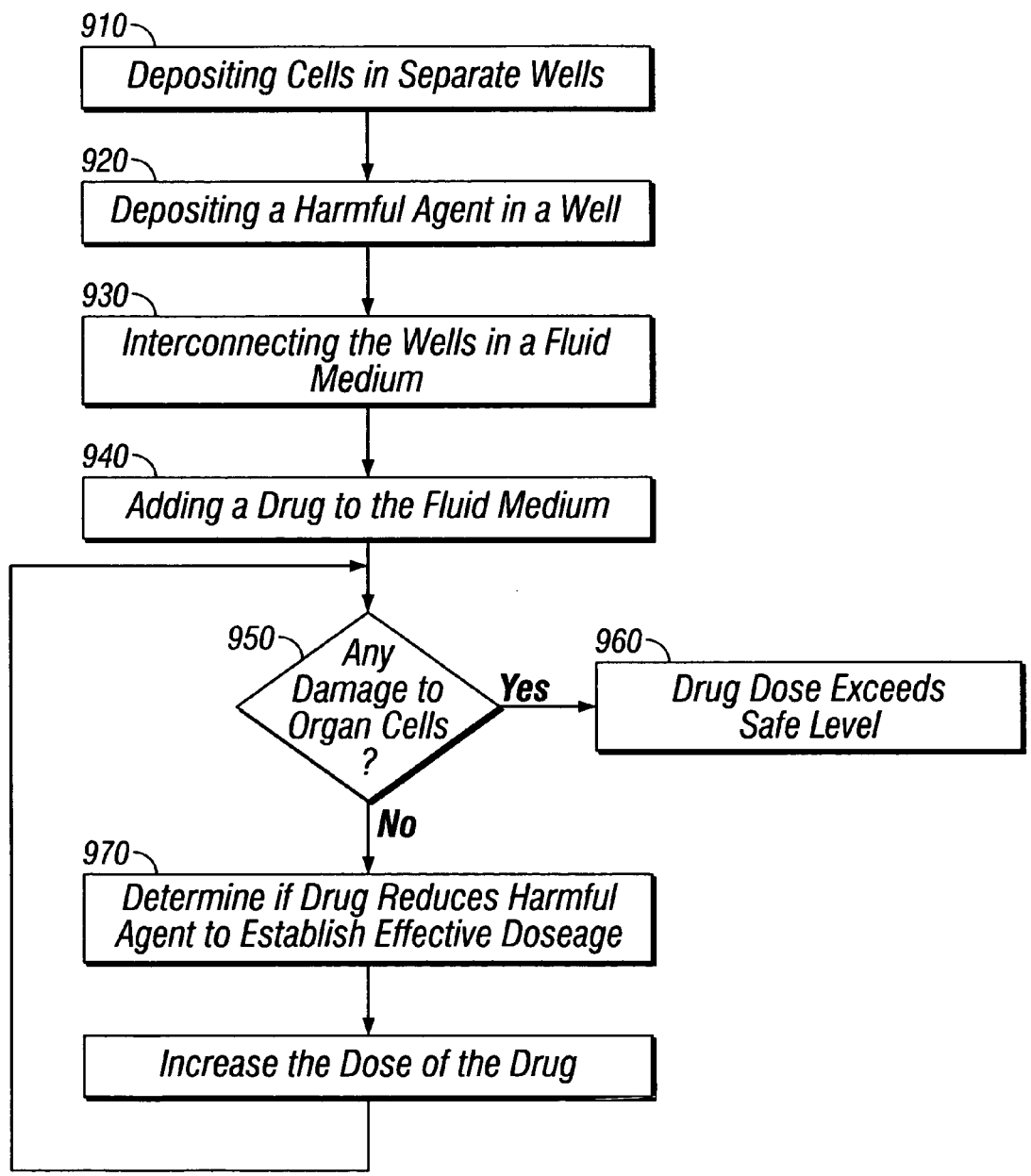
FIG. 9 is a flow diagram of establishing a therapeutic index of a drug.

Referring to FIG. 9, a method 900 of establishing a therapeutic index of a drug includes depositing cells in separate wells of the multi-well plate (operation 910), depositing a harmful agent, such as, for example, tumor cells, in another of the wells (operation 920), interconnecting the wells with a fluid medium (operation 930), and adding a drug to the fluid medium (operation 940).

Safety is evaluated by determining the effect of the drug on the various organ cells (operation 950). If the drug damages any of the organ cells, the drug doseage is deemed to exceed a safe level (operation 960). If the healthy cells are intact, the effect of the drug to reduce the harmful agent is examined. If the harmful agent is reduced, the result is recorded as an effective dose level (operation 970). The dose of the drug is then increased (operation 980) and the process is repeated.

The tool also may be used in a high throughput screening (HTS) process to allow evaluation of a large number of potential drug candidates. In this method, a robotic system is utilized with multi-well plates to perform experimentation. By using a multi-compartment tool as described herein, HTS with co-cultured multiple cell types can be performed for efficacy, toxicity, and metabolism as described above.

Still a further method includes evaluation of co-culture conditions. Some cell types can enhance the culturing of an otherwise difficult to culture cell type. This is routinely performed by trial and error. Using the HTS format, the effects of different cell types on the growth of a difficult to culture cell can be examined. For instance, to evaluate which cells are best to maintain the differentiation of cultured liver cells, liver cells can be co-cultured with cell type 1 (e.g. endothelial cells) in compartment 1; cell type 2 (e.g. 3T3 cells) in compartment 2, and so on. At the end of co-culturing, the properties of the liver cells can be evaluated without complications by the co-cultured cells.

Figure 10:
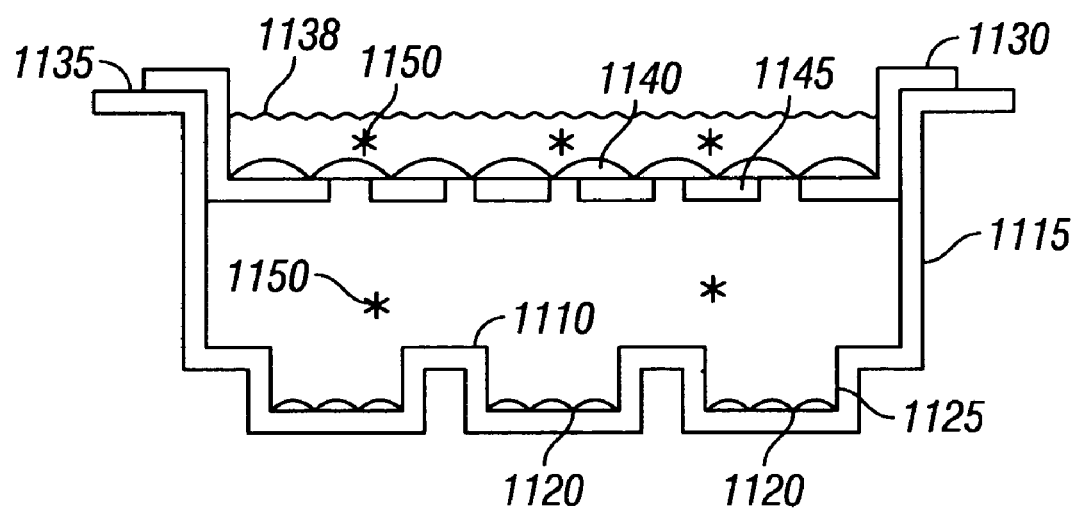
FIG. 10 shows a cell culture tool with an insert tray.

Referring to FIG. 10, a cell culture tool 1000 is shown with an adaptation to measure drug absorption. The cell culture tool 1000 comprises a body 1105 having a substantially planar top surface 1110 surrounded by an outer wall 1115. Six wells 1120 are formed in the body 1105 by depressions in the top surface 1110. Each well 1120 has a containing wall 1125 that is perpendicular to the flat surface 1110.

An insert tray 1130 rests on a lip 1135 at the top of the outer wall 1115. The insert tray 1130 includes a chamber 1138 with a porous membrane 1145 that is positioned inside the outer wall 1115.

Intestinal cells 1140 are placed at the bottom of the chamber 1138 proximate to the membrane. When the tool 1000 is filled, the fluid level rises through the membrane 1140 and a drug 1150 is added to the chamber 1138. The drug 1150 is "absorbed" when it permeates the membrane 1140 to interact with the cells 1120. Thus, the amount of absorption can be measured to simulate absorption of the drug within the intestines.

Since certain changes may be made in the above apparatus and process without departing from the scope of the invention herein involved, it is intended that all matter contained in the above description or shown in the accompanying drawing shall be interpreted in an illustrative and not in a limiting sense. For example, advantageous results still could be achieved if steps of the disclosed techniques were performed in a different order and/or if components in the disclosed systems were combined in a different manner and/or replaced or supplemented by other components. Accordingly, other implementations are within the scope of the following claims.

I claim:

1. A cell culture tool, comprising:
   a body having more than one vessel;
   an outer wall extending from the body to a height above a top edge of each vessel; and
   a partition wall that intersects the body and having opposing ends attached to the outer wall to define more than one chamber, each chamber having a set of more than one vessel that can be fluidly interconnected.

2. The cell culture tool of claim 1, wherein:
   the body further comprises a flat surface; and
   each vessel comprises a depression in the flat surface, the depression configured to contain a volume of fluid.

3. The cell culture tool of claim 1, wherein each vessel comprises a cylindrical bore extending into the body.

4. The cell culture tool of claim 1, wherein the body comprises a rectangular plate surrounded by the outer wall.

5. The cell culture tool of claim 1, wherein each vessel comprises a cup attached to the body, each cup having the top edge below the height of the outer wall.

6. The cell culture tool of claim 1, wherein each vessel comprises a container having a container wall extending to the top edge, the height of the container wall being about 4 millimeters.

7. The cell culture tool of claim 1, wherein the outer wall comprises a height of about 20 millimeters.

8. The cell culture tool of claim 1, wherein each vessel comprises a container having a container wall extending to the top edge, the container wall having a height between 0.1 to 40 millimeters.

9. The cell culture tool of claim 1, wherein the outer wall includes a height between 0.2 to 200 millimeters.

10. A multi-well culture dish, comprising:
- a base having a flat surface with a plurality of wells, each well defined by a containing wall;
- an outer wall surrounding the base, the outer wall having a top edge above a top rim of each containing wall; and
- more than one chamber wall that intersects the base each chamber wall having opposing ends attached to the outer wall to define more than one chamber, each chamber having a plurality of wells that are fluidly isolated from a plurality of wells in any other chamber.

11. The multi-well culture dish of claim 10, wherein the plurality of wells in eat chamber comprises six wells.

12. The multi-well culture dish of claim 10, wherein the wells in each chamber comprise more than two wells.

13. A cell culture tool, comprising:
- a tray having more than one set of wells, each of the wells in the set configured to hold a liquid volume; and
- a containing wall enclosing each set of wells, the containing wall having a height above the top of the wells to fluidly interconnect each set of wells within the containing wall.

14. A cell culture tray, comprising:
- a first compartment with multiple wells, a second compartment with multiple wells and a third compartment with multiple wells;
- wherein the first compartment is configured to hold a liquid volume to fluidly interconnect the multiple wells within the first compartment;
- the second compartment is configured to hold a liquid volume to fluidly interconnect the multiple wells within the second compartment; and
- the third compartment is configured to hold a liquid volume to fluidly interconnect the multiple wells within the third compartment.

15. The cell culture tray of claim 14, wherein the tray comprises:
- a rectangular plate about 12.60 cm long and 8.40 cm wide;
- an outer wall surrounding the plate and extending upward about 0.15 cm; and
- more than one partition wall intersecting the plate to define the first, second and third compartment.

* * * * *